US00RE39650E

(19) United States
(12) Reissued Patent
Mendicino et al.

(10) Patent Number: US RE39,650 E
(45) Date of Reissued Patent: May 22, 2007

(54) SURFACE-ACTIVE ADDITIVES IN THE DIRECT SYNTHESIS OF TRIALKOXYSILANES

(75) Inventors: Frank D. Mendicino, Marietta, OH (US); Kenrick M. Lewis, Rego Park, NY (US); Sebastiano Magri, Termoli (IT); Hua Yu, White Plains, NY (US); Thomas E. Childress, Newport, OH (US)

(73) Assignee: General Electric Company, Schenectady, NY (US)

(21) Appl. No.: 09/488,672

(22) Filed: Jan. 20, 2000

Related U.S. Patent Documents

Reissue of:
(64) Patent No.: 5,783,720
Issued: Jul. 21, 1998
Appl. No.: 08/729,266
Filed: Oct. 10, 1996

(51) Int. Cl.
*C07F 7/04* (2006.01)
*C07F 7/18* (2006.01)

(52) U.S. Cl. ..... 556/470
(58) Field of Classification Search ..... 556/470
See application file for complete search history.

(56) References Cited

U.S. PATENT DOCUMENTS

| | | | | | |
|---|---|---|---|---|---|
| 2,380,997 | A | | 8/1945 | Patnode | 252/225 |
| 2,473,260 | A | | 6/1949 | Rochow | 260/448.8 |
| 3,641,077 | A | | 2/1972 | Rochow | 260/429 R |
| 3,775,457 | A | | 11/1973 | Muraoka et al. | 260/448.8 R |
| 4,113,761 | A | * | 9/1978 | Kreuzburg et al. | 556/470 |
| 4,314,908 | A | | 2/1982 | Downing et al. | 252/182 |
| 4,328,175 | A | | 5/1982 | Roeckel et al. | 261/91 |
| 4,727,173 | A | | 2/1988 | Mendicino | 556/470 |
| 4,761,492 | A | | 8/1988 | Childress et al. | 556/482 |
| 4,931,578 | A | * | 6/1990 | Ohta et al. | 556/470 |
| 4,999,446 | A | | 3/1991 | Moody et al. | 556/470 |
| 5,084,590 | A | | 1/1992 | Ritscher et al. | 556/470 |
| 5,166,384 | A | | 11/1992 | Bailey et al. | 556/466 |
| 5,362,897 | A | * | 11/1994 | Harada et al. | 556/470 |
| 5,527,937 | A | | 6/1996 | Standke et al. | 556/470 |
| 5,728,858 | A | | 3/1998 | Lewis et al. | 556/470 |
| 6,166,237 | A | * | 12/2000 | Simandan et al. | 556/470 |

FOREIGN PATENT DOCUMENTS

| | | |
|---|---|---|
| EP | 0 709 388 A1 | 5/1996 |
| JP | 55-2641 | 1/1980 |
| JP | 55-28928 | 2/1980 |
| JP | 55-28929 | 2/1980 |

OTHER PUBLICATIONS

European Search Report for corresponding European patent application 97117467.7(Jul. 22, 1999)(citing EP 0 709 388 A1).
Suzuki et al., "Direct Synthesis of Trimethoxysilane from Methanol . . . as a Catalyst", The Chemical Society of Japan, Bull. Chem. Soc. Jpn., 64, 3445–3447 (Nov. 1991).
Abstract of Japanese patent Jpn. Kokai Tokkyo Koho 55–76, 891 (1980), "Methoxysilanes", taken from Chemical Abstracts, vol. 94, p. 744 (1981).
Abstract of Japanese patent Jpn. Kokai Tokkyo Koho 62–96, 433 (1987), "Alkoxysilanes", taken from Chemical Abstracts, vol. 107, p. 721 (1987).
S. Ross, "Mechanisms of Foam Stabilization and Antifoaming Action," Chemical Engineering Process, vol. 63, No. 9, pp. 41–47 (Sep. 1967).
Ross and Nishioka, "Experimental Researches on Silicone Antifoams," Emulsions, Latices and Dispersions, Ed. Paul Becher and Marvin N. Yudenfreund, Marcel Dekker, Inc. (New York and Basel), pp. 237–256 (1978).
Boutevin and Pietrasanta, "The Synthesis and Applications of Fluorinated Silicones, Notably in High–Performance Coatings", Progress in Organic Coatings, 13, pp. 297–331 (1985).
Ramachandran and Chaudhari, Three–Phase Catalytic Reactors, Gordon and Breach Science Publishers (New York, London Paris), Table of Contents, pp. v–viii (1983).
Gartsman et al., "Mass Transfer with Chemical Reaction in the Three–Phase System Gas–Liquid–Solid Catalyst," International Chemical Engineering, vol. 17, No. 4, pp. 697–702 (Oct. 1977).
Satterfield and Huff, "Effects of Mass Transfer of Fischer–Tropsch Synthesis in Slurry Reactors", Chemical Engineering Science, vol. 35, pp. 195–202 (1980).
Ying et al., "Gas Holdup in Gas–Liquid and Gas–Liquid–Solid Flow Reactors", Ind. Eng.Chem. Process Des. Dev., 19, pp. 635–638 (1980).
Boxall, et al., "Oxygen Reactor for the Goethite–Zinc Leach Residue Process", Journal of Metals, pp. 58–61 (Aug. 1984).
Brunet et al., "Sol–Gel Polymerization Studied through 29Si NMR with Polarization Transfer", J. Phys. Chem., 95, pp. 945–951 (1991).
Brunet and Cabane, "Populations of Oligomers in Sol–Gel Condensation", Journal of Non–Crystalline Solids, 163, pp. 211–225 (1993).
Bendall, R., "Depth and Refocusing Pulses Designed for Multipulse NMR with Surface Coils", Journal of Magnetic Resonance, 53, pp. 365–385 (1983).
The Analytical Chemistry of Silicones, Ed. A. Lee Smith, John Wiley & Sons, Inc. (New Yor,k Chisheser, Brisbane, Toronto, Singapore), Table of Contents, pp. ix–xiv (1991).
Abstract of Japanese patent Jpn. Kokai Tokkyo Koho 57–108,094 (1982), "Alkoxysilanes", taken from Chemical Abstracts, vol. 98, p. 524 (1983).

(Continued)

*Primary Examiner*—Samuel Barts

(57) ABSTRACT

Disclosed is a process in which surface-active additives are used in the slurry phase Direct Synthesis of trialkoxysilanes to shorten the period between the start of the reaction and the attainment of steady-state rates and selectivities, to improve product yields and to control or prevent foam formation. Compositions comprising silicone antifoam compounds and fluorosilicone polymers are the preferred surface-active additives of the instant process.

22 Claims, 1 Drawing Sheet

OTHER PUBLICATIONS

Silicon for Chemical Industry, Ed. H.A. Oye and H. Rong, Tapir Publishers, Norwegion Institute of Technology, Table of Contents, 4 pages (Jun. 3–5, 1998).
Silicon for Chemical Industry, Ed. H.A. Oye and H. Rong, Tapir Publishers, Norwegion Institute of Technology, Table of Contents, 3 pages (Jun. 8–10, 1994).
Silicon for Chemical Industry, Ed. H.A. Oye and H. Rong, Tapir Publishers, Norwegion Institute of Technology, Table of Contents, 3 pages (Jun. 16–18, 1992).
Silicon for Chemical Industry, Ed. H.A. Oye and H. Rong, Tapir Publishers, Norwegion Institute of Technology, Table of Contents, 3 pages (Jun. 18–20, 1996).

* cited by examiner

SURFACE-ACTIVE ADDITIVES IN THE DIRECT SYNTHESIS OF TRIALKOXYSILANES

Matter enclosed in heavy brackets [ ] appears in the original patent but forms no part of this reissue specification; matter printed in italics indicates the additions made by reissue.

FIELD OF THE INVENTION

The invention relates to the production of trialkoxysilanes in the catalyzed Direct Reaction of silicon metal with alcohols. In particular, the process entails the addition of surface-active agents to the slurry comprising solvent, silicon and catalyst to shorten the period between the start of the reaction and the attainment of steady-state rates and selectivities, to improve product yields and to control or prevent foam formation during the Direct Synthesis of trialkoxysilanes.

BACKGROUND OF THE INVENTION

Trialkoxysilanes, especially trimethoxysilane and triethoxysilane, are used in the production of silane coupling agents. One method of synthesis of trialkoxysilanes is directly from silicon and an alcohol. This method is known variously in the art as the Direct Synthesis, the Direct Reaction, the Direct Process or the Rochow Reaction. For trialkoxysilanes, it is most conveniently performed in slurry reactors.

In a slurry reactor for the Direct Synthesis of trialkoxysilanes, catalytically-activated silicon particles are maintained in suspension in a thermally stable, high boiling solvent and are made to react with an alcohol at an elevated temperature. This type of reaction is disclosed by Rochow in U.S. Pat. No. 3,641,077. The patent teaches preparation of trialkoxysilanes by directly reacting copper-silicon mass, suspended in a silicone oil, with alcohol at 250°–300° C. The copper-silicon mass contains about 10 weight percent copper and is prepared by heating copper and silicon above 1000° C. in a furnace in a stream of hydrogen gas. This method results in low yields of trialkoxysilanes.

U.S. Pat. No. 3,775,457 teaches the use of polyaromatic hydrocarbon oils as solvents in the Direct Synthesis of trialkoxysilanes from an alcohol and finely divided silicon metal activated with cuprous chloride catalyst. Although the use of cuprous chloride results in increased yield over that obtained using the sintered copper-silicon mass of U.S. Pat. No. 3,641,077, the use of cuprous chloride catalyst also results in the formation of HCl which, in turn, necessitates the use of costly corrosion resistant materials of construction for the reactor and its ancillary equipment. Further, the presence of chloride in the reactor and in the product stream reduces the yield of trialkoxy-silane by catalyzing the consecutive reaction of trialkoxysilane with the alcohol to yield tetra-alkoxysilanes.

Additionally, when methanol is a reactant, the HCl resulting from the use of the cuprous chloride catalyst will react with some of the methanol to produce methyl chloride and water. This loss of methanol to an undesirable side reaction makes the cuprous chloride catalyzed reaction inefficient. Moreover, water produced by this reaction can react with trialkoxysilanes and tetraalkoxysilanes to produce soluble and gelled siloxanes and further reduce the efficiency of the Direct Process. The presence of water in the reaction mixture can also inhibit the sustained conversion of silicon metal to desirable products at economically beneficial rates.

Other patents, for example Japenese Kokai Tokkyo Koho 55-28928 (1980), 55-28929 (1980), 55-76891 (1980), 57-108094 (1982) and 62-96433 (1987), which disclose the use of cuprous chloride and cupric chloride and alkylated benzene solvents such as dodecylbenzene and tridecylbenzene, are subject to these same limitations. It is desirable to use the alkylated benzenes because they are less expensive and less hazardous to people and the environment than the polyaromatic hydrocarbon solvents of U.S. Pat. No. 3,775,457.

U.S. Pat. No. 4,727,173 discloses that the use of copper (II) hydroxide as catalyst avoids the limitations associated with cuprous chloride and provides a high selectivity to trialkoxysilanes. The preferred solvents are diphenyl ether, polyaromatic hydrocarbons like THERMINOL® 59, THERMINOL® 60 and THERMINOL® 66, and alkylated benzenes such as dodecylbenzene. However, when copper (II) hydroxide is used in combination with alkylated benzene solvents, such as dodecylbenzene, the Direct Synthesis of trialkoxysilanes becomes unstable after approximately 25–35 weight percent of the silicon has been reacted. When methanol is the alcohol reactant at temperatures above about 220° C., the trimethoxysilane content in the reaction product declines from approximately 90–95 weight percent to approximately 50–60 weight percent and recovers again to between 80–95 weight percent after about 60 percent silicon conversion. Simultaneous with this loss of selectivity is the enhanced formation of methane, water and dimethyl ether. Methane and dimethyl ether formation represent inefficient use of the methanol reagent. Problems attendant to the generation of water in the reaction mixture have been recited hereinabove.

Alcohol dehydration and dehydrogenation are especially troublesome problems when ethanol and other higher homologs are used in the Direct Synthesis. At some temperatures (>250° C.), alkenes and aldehydes, and not the desired trialkoxysilanes, are formed in significant amounts. Even when these are not the predominant products, their presence in the reaction mixture can result in the inhibition of further catalytic activity. At lower temperatures, (for example 220° C.) alcohol decomposition reactions are less prevalent, but the Direct Synthesis is impractically slow. Japanese Kokai Tokkyo Koho 55-2641 (1980) discloses the use of cyclic ethers to improve reactivity and selectivity to triethoxysilane when the Direct Synthesis is conducted in dodecylbenzene at these lower temperatures. Cyclic ethers such as dibenzo-18-crown-6 are quite expensive; others such as 12-crown-4 are also toxic.

U.S. Pat. No. 5,527,937 (European Patent application EP 0709388 A1) discloses a process for the Direct Synthesis of triethoxysilane and trimethoxysilane, wherein CuCl is the catalyst, tri- and tetra-toluenes and/or their alkyl substituted derivatives are the solvents and dimethylsilicone oils are antifoaming agents. The polyphenyl solvents of this process are expensive heat transfer fluids.

Foaming problems are also disclosed in Example 3 of U.S. Pat. No. 3,775,457 (German Patent 2,247,872). Foaming can lead to the partial or complete discharge of the reaction slurry from the reactor into the distillation and receiving vessels attached thereto. This is not only operationally inefficient with respect to raw material usage, but it also presents a difficult and time-consuming cleanup problem in laboratory, pilot and commercial scale reactions.

Thermal activation of slurries containing copper catalysts and silicon is disclosed in a number of patents, for example, U.S. Pat. Nos. 3,775,457 and 4,727,173. Use of hydrogen to activate silicon with copper for the Direct Reaction has been disclosed in U.S. Pat. Nos. 2,380,997; 2,473,260; 3,641,077; and 4,314,908. Hydrogen activation, as taught in these patents, is accomplished at temperatures above about 400° C. in fixed bed reactors, fluidized bed reactors or furnaces with silicon—copper catalyst mixtures containing more than 1.5 weight percent copper. No teaching is given regarding selectivity, reactivity and reaction stability of the silicon—copper masses in the slurry phase Direct Synthesis of trialkoxysilanes.

Suzuki, et al. (Bulletin of the Chemical Society of Japan, vol. 64 (1991) pp 3445–3447) disclosed that hydrogen activation of silicon—$CuCl_2$ mixtures (2.5 wt % Cu) in a fixed bed at 260° C. afforded complete silicon conversion and high (89%) selectivity to trimethoxysilane in a fixed bed Direct Reaction with methanol. The duration of the induction period, the reaction rate and selectivity to trimethoxysilane were all very dependent on the temperature of hydrogen activation.

Thus, there continues to exist the need for a stable, highly selective and rapid Direct Synthesis of trialkoxysilanes which is conducted in cheaper, less hazardous solvents and yet avoids the above-mentioned deficiencies of copper chlorides and alkylated benzenes. In particular, there is a need for such a Direct Synthesis which eliminates or avoids the alcohol reduction and alcohol dehydration side reactions. These needs are addressed in a copending patent application filed on even date herewith and assigned to the assignee of the present application, bearing internal file number 89603 and entitled "Activation of Copper-Silicon Slurries for the Direct Synthesis of Trialkoxysilanes".

There is also a need for a Direct trialkoxysilane Synthesis process in which foaming is controlled so that the reaction slurry is retained in the reactor. Moreover, the foam control method(s) must not have any deleterious effect(s) on the selectivity, rate and stability of the Direct Synthesis of trialkoxysilanes and must remain effective throughout the entire course of the reaction, especially when the solvent is used for more than one charge of silicon, when recycled solvent is used, or when the Direct Process is conducted continuously.

OBJECTS OF THE INVENTION

It is therefore an object of the invention to provide a process for producing trialkoxysilane directly from silicon metal and alcohol which results in a high trialkoxysilane to tetraalkoxysilane ratio in the product over the entire course of the reaction.

Another object of the invention is to provide such a highly selective process while avoiding foaming and its attendant problems.

Another object of the invention is to provide such a Direct Synthesis process which results in a high conversion of silicon metal into trialkoxysilane product and which results in little unreacted silicon content in the solid reaction residue.

A still further object is to provide such a Direct Synthesis process in which there is only a short delay between the start of the reaction and the attainment of high, stable reaction rates and selectivities.

A further object of the invention is to provide such a Direct Synthesis process which does not require the use of costly corrosion resistant materials in the construction of the process apparatus.

SUMMARY OF THE INVENTION

The present invention provides a process for producing trialkoxysilane of the formula $HSi(OR)_3$, wherein R is an alkyl group containing from 1 to 6 carbon atoms inclusive, which process comprises:

(a) slurrying silicon metal in a thermally stable solvent, preferably an alkylated benzene or polyaromatic hydrocarbon solvent, in the presence of a catalytically effective amount of a copper catalyst precursor and of a surface-active additive hereinafter defined and, optionally, an alcohol of formula ROH; (b) activating said catalyst precursor, for instance by heating and agitating this slurry, and/or optionally injecting into it nitrogen and/or other inert gas, and/or injecting into the slurry a reducing agent such as hydrogen, carbon monoxide or monosilane or reducing gases containing them, to reduce non-zerovalent copper present to zerovalent copper, to produce a copper-activated silicon slurry; (c) reacting this copper-activated silicon slurry with an alcohol of the formula ROH to produce said trialkoxysilane; and (d) recovering said trialkoxysilane from the reaction product.

The present process prevents significant foam formation and affords good reaction stability. The surface-active agents used for foam control also effect a reduction in the time from the start of the reaction to the attainment of stable rates and selectivities. The process produces trialkoxysilanes at high rates and in quantity such that the gravimetric ratio of trialkoxysilane to tetraalkoxysilanes are greater than about 9 to 1 when calculated over the entire course of the reaction. Furthermore, the use of copper catalyst precursor as defined herein, hydrogen and the organosilicone and/or fluorosilicone surface-active additives does not generate corrosive materials and, thus costly materials of construction are not required for the reactor. The process of the invention also results in high overall conversion of silicon and alcohol to desirable products.

DETAILED DESCRIPTION OF THE INVENTION

Figure 1:
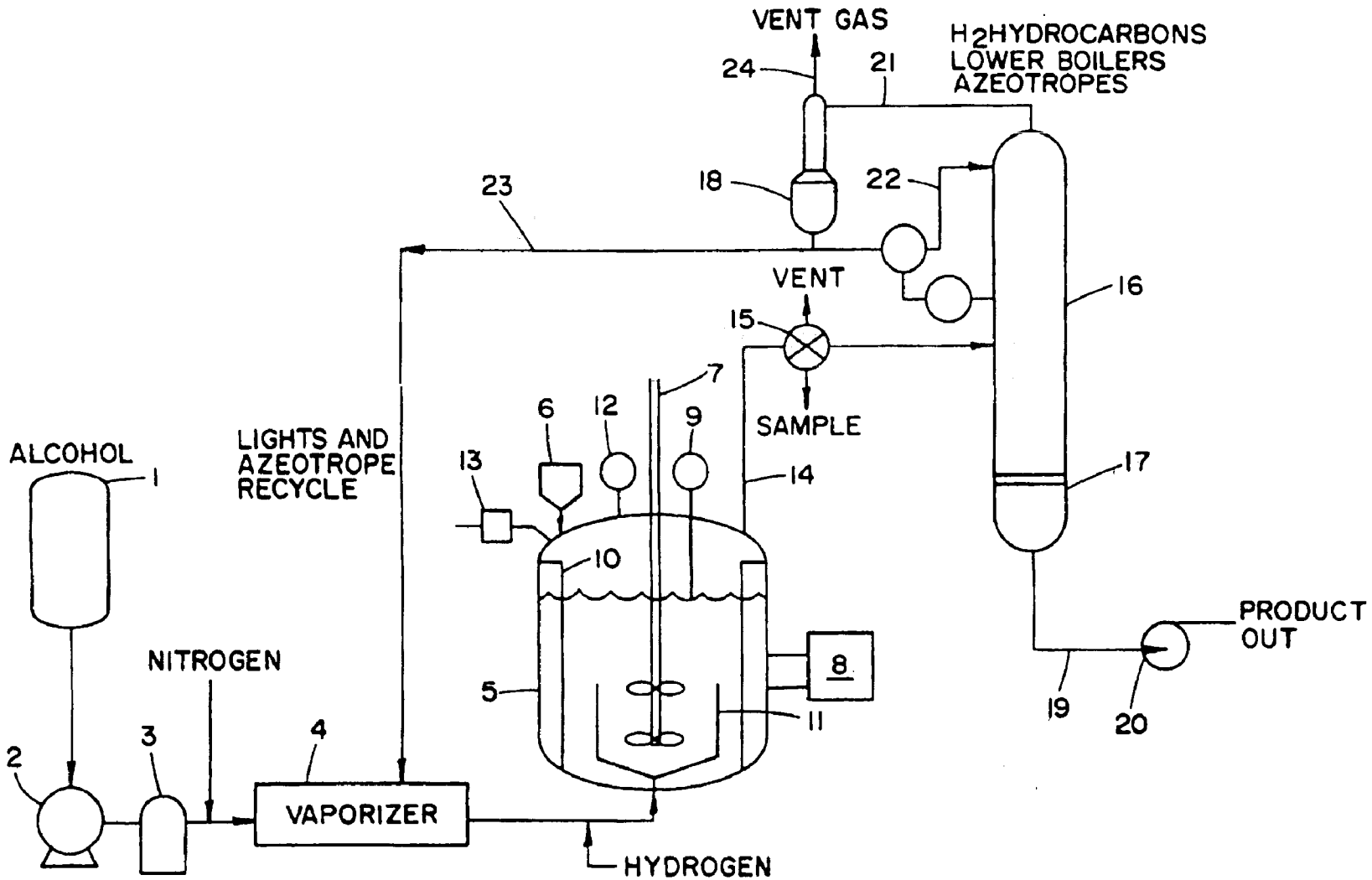
FIG. 1 is a flowchart of a useful embodiment of the process of the present invention.

The following equations are representations of the principal chemical reactions occurring during the Direct Synthesis of trialkoxysilanes.

$$Si+3ROH \rightarrow HSi(OR)_3+H_2 \quad [1]$$

$$HSi(OR)_3+ROH \rightarrow Si(OR)_4+H_2 \quad [2]$$

$$ROH+H_2 \rightarrow RH+H_2O \quad [3]$$

$$2ROH \rightarrow ROH+H_2O \quad [4]$$

$$RCH_2OH \rightarrow R'CH{=}CH_2+H_2O \quad [5]$$

$$2Si(OR)_4+H_2O \rightarrow (RO)_3SiOSi(OR)_3+2ROH \quad [6]$$

$$2HSi(OR)_3+H_2O \rightarrow H(RO)_2SiOSi(OR)_2H+2ROH \quad [7]$$

$$2HSi(OR)_3+Si(OR)_4+H_2O \rightarrow HSiO(RO)_2SiOSi(OR)_2OSi(OR)_2H+2ROH \quad [8]$$

The desirable products of the instant Direct Synthesis are trialkoxysilanes of general formula. $HSi(OR)_3$, wherein R is an alkyl group of 1 to 6 carbon atoms. R is preferably methyl and ethyl. Byproducts of the synthesis are $Si(OR)_4$, $RSiH(OR)_2$, $RSi(OR)_3$, linear, branched and cyclic silicates such as $(RO)_3SiOSi(OR)_3$, $H(RO)_2SiOSi(OR)_2H$, $HSi(RO)_2SiOSi(OR)_3$, $(R(O)_3SiOSi(OR)_2R$, $(RO)_3SiOSi(RO)_2OSi$ $(RO)_3$, $(RO)_3SiOSi(OR)HOSi(OR)_3$, $(RO)_3SiOSi(OR)ROSi(OR)_3$, $(RO)Si[OSi(OR)_3]_3$, $(RO)_3SiOSi(OR)(OSi(RO)_3)OSi(OR)_3$, and $[OSi(OR)_2]_n$, (n4, 5 . . . ), hydrogen gas, hydrocarbons (RH) such as methane and ethane, alkenes ($R'CH{=}CH_2$) such as ethylene and ethers (ROR) such as dimethyl ether and diethyl ether. In the general formula, $R'CH{=}CH_2$, for the alkene byproducts. R' is hydrogen or an alkyl group of 1 to 4 carbon atoms. Hydrogen gas, hydrocarbons and the ethers are typically not condensed in the cold trap with the liquid products and exit the apparatus as a gaseous stream. Some of the silicates are volatilized out of the reactor and are soluble in the liquid reaction product. Other remain solubilized in the solvent or precipitate as insoluble gels.

When the Direct Synthesis is conducted pursuant to the present invention, trialkoxysilanes comprise at least 80 weight percent, preferably at least 85 weight percent, of the liquid reaction products. Typical levels of the alkyl silicates, $Si(OR)_4$, are less than 9 weight percent, preferably less than 6 weight percent. $RSiH(OR)_2$ and $RSi(OR)_3$ compounds are individually less than 2 weight percent and preferably less than 1 weight percent. Condensed silicates are maximally 1 weight percent and preferably less than 0.5 weight percent. In addition to the percentage ranges taught hereinabove, selectivity to the desired trialkoxysilanes may also be expressed as the gravimetric ratio, $HSi(OR)_3/Si(OR)_4$. By the method of the instant invention, this ratio is at least 9 when computed over the total course of a reaction. It is preferably at least 15 and may attain values greater than 30 during the steady-state portion of the reaction.

Gas chromatographic (GC) analysis has been found to be a reliable and accurate technique to quantify the composition of the liquid reaction product. Other methods such as nuclear magnetic resonance (NMR) and mass spectrometry (MS) may also be used. These are particularly useful for identifying and quantifying the higher molecular weight silicates contained in the reaction product and reaction solvent. Data on the composition and weight of the reaction product and the fraction of silicon in each of the components are used to calculate the silicon conversion. Reaction rate is typically expressed as silicon conversion per unit time.

In the nomenclature of silicon chemistry, silicon atoms bonded to four oxygen atoms are designated Q groups. $Q^0$ represents the monomers, $Si(OR)_4$. $Q^1$ designates the groups, $OSi(OR)_3$, at the ends of chains; $Q^2$ denotes internal groups, $OSi(OR)_2O$, in chains or cyclics; $Q^3$ refers to branching sites, OSiO(OR)O, and $Q^4$ to fully crosslinked groups, $Si(OSi)_4$. These groups have characteristic $^{29}Si$ NMR chemical shifts within the range, −70 to −120 ppm whose assignments are facilitated by the use of DEPT and depth pulse analysis. Publications by Brunet, et, al. (Journal of Physical Chemistry, vol. 95 (1991), pp 945–951; Journal of Non-Crystalline Solids, vol. 163 (1993) pp 211–225) and Bendall, et al. (Journal of Magnetic Resonance, vol. 53 (1983) 365–385) detail the use of these NMR analytical techniques.

The gaseous product stream contains hydrogen gas, hydrocarbons, ethers and inerting agents such as nitrogen or argon. Analytical methods based on gas chromatography, Fourier Transform Infra-red spectroscopy (FTIR) or mass spectrometry may be used to identify and quantify these components in the gaseous effluent. Assuming that the reaction of Equation [1] produces most of the hydrogen gas in the effluent, the hydrogen generated in the Direct Synthesis can be used as an approximate measure of reaction rate and silicon conversion. Hydrocarbon and ether formation depicted in Equations [3–5] can be used as a measure of the inefficiency of alcohol conversion. It is desirable less than 2 weight percent of the alcohol fed to the reaction be converted to hydrocarbons and ethers and most desirable than none be so converted.

CATALYST PRECURSORS

Copper and halogen-free copper compounds which are readily reduced to copper by hydrogen, alcohols, organosilanes containing SiH, $SiH_2$ or $SiH_3$ groups, monosilane, carbon monoxide and/or heating in polyaromatic hydrocarbons, are useful as catalyst precursors of this inventive process. Suitable examples are metallic copper powders, including those produced by supercritical processes and metal atom vaporization, or in situ in the reaction slurry of the Direct Synthesis, copper colloids, copper oxides, copper hydroxides, mixed hydrous oxides such as $3\ CuO.Cu(OH)_2$, copper alkoxides (typically of the formula $Cu(OA)_{1-2}$ wherein A is alkyl containing 1 to 6 carbon atoms, for example, $Cu(OCH_3)_2$, $Cu(O\text{-}tC_4H_9)$) and carboxylates (typically of the formula $Cu(OOA)_{1-2}$ wherein A is as defined herein, for example, $Cu(OOCH)_2$, $Cu(OOCCH_3)_2$). All polymorphic forms of copper (II) hydroxide, particularly the cubic and orthorhombic polymorphs, are preferred catalyst precursors of the instant invention.

The copper catalyst precursor used in the process of this invention is present in an amount effective to catalyze the reaction upon activation. Generally an effective amount ranges from about 0.01 to about 5 parts by weight of catalyst precursor per 100 parts by weight of the silicon metal. Usually the amount of catalyst precursor will be from about 0.1 to about 2.6 parts by weight per 100 parts by of the weight silicon metal. The preferred amount of copper catalyst precursor is from about 0.1 to about 1.0 parts by weight per 100 parts by weight silicon metal.

Copper (II) hydroxide used in the present invention is preferably anhydrous, but material containing water of hydration is also usable. The water content of commercial copper (II) hydroxide may be as high as 20 weight percent. If a hydrated catalyst precursor is used, provision must be made in the design of the apparatus to avoid contact of the water formed during its reduction and thermal decomposition with the trialkoxysilane reaction product.

In addition to water content, various other criteria can be used to characterize the copper catalysts and catalyst precursors of this invention. Surface area of the catalyst precursor can be as low as 0.1 $m^2/g$. Areas in the range 10–50 $m^2/g$ are preferred. Particle size of the copper catalyst precursor can be from less than 1 micron up to about 100 microns. The desirable range is 0.1–50 microns and the preferred range 0.1–30 microns.

The presence of excessive tin in the reaction has adverse effects on the reaction rate and/or the selectivity for trialkoxysilane and so such excessive tin levels should be avoided. It is desirable that the tin content of the catalyst precursor (and the catalyst itself) be less than 1000 parts per million, preferable that it be less than 300 parts per million and most preferable that it be less than 100 parts per million. Gravimetry and atomic absorption spectroscopy are suitable methods for quantifying the silicon content of the reaction solvent. Analytical procedures are published, for example, in The Analytical Chemistry of Silicones, (A. L. Smith, Editor), John Wiley & Sons Inc., NY, 1991, chapter 8. Soluble silicates retained in the reaction solvent are a measure of the extent to which side reactions such as those in equations 6–8 have occurred. All of these reactions depend on the presence of water, which is formed, for example, by the reaction of Equations [3–5]. Gels and soluble silicates contained in the reaction solvent can be removed with boric acid and borates according to the method disclosed by Bailey, et al. in U.S. Pat. No. 5,166,384, which is hereby incorporated by reference.

Of greater importance is the tin content of the reaction slurry. Based on the weight of silicon at the outset of a reaction, it is desirable that the tin content be less than 100 parts per million and preferable that it be less than 10 parts per million.

Zinc content of the catalyst precursor is desirably less than 2500 parts per million and preferably less than 1500 parts per million. Based on the initial weight of silicon charged to the reactor, the zinc content of the reaction slurry must be less than 100 parts per million, and preferably less than 50 parts per million. Other critical trace elements which are ordinarily contained in the catalyst precursor are lead (Pb) and chloride ($Cl^-$). Their concentrations in the slurry must be <50 parts per million and <100 parts per million, respectively. We have determined that copper halide compounds such as CuCl and $CuCl_2$ are effective catalyst sources when employed with the surface-active agents in the process of this invention. The chloride restriction above arises not from catalytic inefficiency or ineffectiveness, but from its impact on reactor corrosion.

SILICON

The silicon metal reactant used in the process of this invention can generally be any commercially available grade of silicon in particulate form. It may be produced by any of the methods in current practice such as casting, water granulation, atomization and acid leaching. These methods are more fully described in *Silicon for the Chemical Industry,* vols. I, II III, (H. Oye, et al. Editors), Tapir Publishers, Norwegian Institute of Technology. A typical composition of commercial silicon metal useful in this invention expressed in percent by weight, is Si~98.5%, Fe<1%, Al~0.05 to 0.7%, Ca~0.001 to 0.1%; Pb<0.001%, Water<0.1%. Generally, smaller particle sizes are preferred for ease of dispersion in the slurry, faster reaction and minimization of erosion in the reactor. Sieving of ground silicon to regulate particle size is optional. An unsieved sample with particle sizes from <45 microns to >600 microns performed as satisfactorily as a sieved one with particle sizes in the narrower range of 75–300 microns.

ALCOHOL

The alcohols which are useful in the process of this invention are those of the formula ROH wherein R is an alkyl group containing from 1 to 6 carbon atoms, inclusive. Preferable R is an alkyl group containing from 1 to 3 carbon atoms inclusive. The most preferred alcohols are methanol and ethanol. While it is customary to use a single alcohol in the Direct Process, mixtures of two or more may also be used to prepare trialkoxysilanes with different alkoxy groups, or to facilitate the reaction of a less reactive alcohol. For example, about 5 weight percent methanol may be added to ethanol to improve the rate and stability of the Direct Synthesis of triethoxysilane. Alternatively, reaction may be initiated with one alcohol and continued with another, or with a mixture. Thus, a hydrogen activated slurry may be reacted initially with methanol prior to the Direct Reaction with ethanol.

Generally, the reaction is run batchwise in a slurry and the alcohol is fed into the slurry as a gas or liquid. Gaseous introduction is preferred. An induction period lasting from a few minutes up to about five hours may be observed. The initial alcohol feed rate is optionally controlled at a low level and increased following the induction period. Similarly, the alcohol feed rate is optionally reduced after about 70 weight percent silicon conversion to minimize the formation of tetraalkoxysilanes. Generally, once the reaction is running, the alcohol feed rate can be adjusted to give the desired level of methanol conversion. One skilled in the art can readily adjust the feed rate in a given reaction run by monitoring the product composition. If the feed rate is too high the product stream will contain a larger proportion of unreacted alcohol. It is preferable that the alcohol be anhydrous. However, water contents of up to 0.1 weight percent can be tolerated without significant loss of selectivity, reactivity and stability.

SOLVENT

The solvents useful in the process of this invention are inert solvents that do not degrade under the activation and reaction conditions. The preferred solvents are high temperature stable organic solvents typically used as heat exchange media. Examples include THERMINOL® 59, THERMINOL® 60, Therminol® 66, DOWTHERM® HT, MARLOTHERM® S, MARLOTHERM® L, diphenyl ether, diphenyl, terphenyl and alkylated benzenes, alkylated diphenyls and alkylated terphenyls with normal boiling points higher than about 250° C.

THERMINOL ® is the Monsanto Company trade name for heat transfer fluids. THERMINOL ®59 is a mixture of alkyl-substituted aromatic compounds recommended for use between −45° to 315° C. THERMINOL® 60 is a mixture of polyaromatic compounds with an average molecular weight of 250. Its optimum temperature range is from −45° to 315° C. THERMINOL® 66 and DOWTHERM ® HT are mixtures of hydrogenated terphenyls with an average molecular weight of 240. Maximum temperature limit is about 370° C. THERMINOL ®59, THERMINOL® 66 and DOWTHERM® HT are preferred solvents of this invention. DOWTHERM® fluids are produced by Dow Chemical Company.

MARLOTHERM® is the Hüls AG trade name for its heat transfer fluids. MARLOTHERM® S is a mixture of isomeric dibenzylbenzenes. MARLOTHERM® L is a mixture of isomeric benzyl toluenes. Both can be used at temperatures up to about 350° C. Both are preferred solvents for the instant invention.

Suitable alkylated benzenes are dodecylbenzene, tridecylbenzene, tetradecyl-benzene and their mixtures such as are sold by Vista Chemical Company under the trade name NALKYLENE®, NALKYLENE® 550BL, NALKYLENE ®550 L and NALKYLENE® 600 L are particularly preferred solvents of this invention. When reductive activation of the copper catalyst precursor—silicon mixture is practiced in an alkylated benzene solvent and the resulting slurry reacted with methanol vapor, no loss of selectivity to trimethoxysilane is observed between 25–35 weight percent silicon conversion. Mixtures of alkylated benzenes and polyaromatic hydrocarbons are also useful solvents for the instant invention. Used solvents can be treated with boric acid and borates as described in U.S. Pat. No. 5,166,384 and reused in subsequent reactions.

Silicon metal, catalyst, surface-active additive and solvent can be added together in the reactor in any order. The solvent is present in an amount sufficient to disperse the solid and gaseous reactants homogeneously. Generally, reactions are initiated with solvent and solids in a gravimetric ratio between 1:2 and 4:1, preferably 1:1 to 2:1. However, as the silicon is consumed during batchwise Direct Synthesis, the solvent to solids ratio will increase. The ratio can be maintained within narrow limits of the preferred range for continuous reactions.

SURFACE-ACTIVE ADDITIVE

The surface-active additives of the instant invention are compositions comprising hydrophobized solids (usually silica) and either or both of (a) organopolysiloxanes commonly called antifoam compounds, and/or (b) organofluoropolysiloxanes. The term "foam control agent" is sometimes used in the art to describe these compositions. It refers both to surface-active materials that eliminate foam (i.e., defoamers) and to those that prevent foam formation (i.e., antifoams). Some surface-active materials demonstrate both properties. Foam control agents are preferably added to the reaction slurry at the outset of the Direct Synthesis. However, additional amounts, especially of defoamers, may also be introduced continuously or intermittently, if required, while the reaction is in progress. It is desirable that the foam control agent be used in an amount which is effective and durable. The foam control additive must be thermally stable and effective under the reaction conditions and must not introduce any agents which are inhibiting or poisonous to the Direct Process into the reaction slurry.

In addition to foam control, the surface-active additive shortens the period between the start of the reaction and the attainment of maximum rate and selectivity. Thus, more efficient conversion of silicon and alcohol raw materials to higher yields of trialkoxysilanes are realized. Sometimes, as in the Direct Synthesis of triethoxysilane in MARLOTHERM® S with the fluorosilicone. FS 1265, as surface-active additive, this period may not be shortened compared to the control experiment without FS 1265, but the steady-state rate and selectivity in the presence of the surface-active additive are considerably higher than in the control. This behavior also results in higher yields of the desired trialkoxysilane.

Basic information on the preparation of antifoam compounds can be found in S. Ross, Chemical Engineering Process, vol. 63 (September 1967) p 41 and in S. Ross and G. Nishioka, Emulsions, Latices and Dispersions, p237, (1978). Typically, antifoam compounds contain hydrophobized silica particles with average particle sizes in the range, 0.2–5 microns, and specific surface areas between 50 and 400 square meters per gram. In general, the antifoaming effectiveness tends to increase with the content of hydrophobized silica in the antifoam compound. The organopolysiloxane may be a linear oligomer or polymer of the general formula: $R''_3SiO—(SiR''_2O)_a—SiR''_3$, a cyclic of the general formula: $(R''_2SiO)_b$, or a branched oligomer or polymer of the type:

$$\begin{array}{l} R''_3SiO—(SiR''_2O)_k—(SiR''O)_r—SiR''_3 \\ \qquad\qquad\qquad\qquad\quad | \\ \qquad\qquad\qquad\qquad (OSiR''_2)_s—SiR''_3 \end{array}$$

wherein R" in each occurrence is the same or different and each R" is a $C_1$–$C_{20}$ (preferably $C_1$–$C_{12}$) alkyl, phenyl, alkyl-substituted alkyl, cycloalkyl, or alkyl-substituted cycloalkyl group, such as methyl, ethyl, phenyl, tolyl, cyclohexyl and methylcyclohexyl. The subscripts, a, b, k, r and s are greater than zero and have the values such that the normal boiling point of the organopolysiloxane is at least 10° C. higher than the temperature of the Direct Synthesis slurry. The organopolysiloxane is preferably used with hydrophobized silica, at a weight ratio of 1:99 to 99:1.

Suitable examples for use with instant invention include the OSi Specialties products, SAG® 47, SAG® 100 and SAG® 1000. These may be mixed with the reaction solvent, or another thermally stable carrier, prior to addition to the reaction slurry. Under Direct Synthesis conditions, the effective quantities depend on factors such as the alcohol feed rate, the specific alcohol employed, the reactor pressure, the specific solvent, the concentration of condensed silicates in the slurry and the intrinsic antifoaming properties of the antifoam compound. For example, more foam is generated at higher alcohol feed rates than at lower values. Usually, foaming becomes evident in the first few minutes after alcohol injection and, later after the reaction has been in progress for some time, when the soluble silicate concentration has increased beyond a threshold level. An increase of reactor pressure (from atmospheric up to 2 atmospheres) will sometimes temporarily collapse the foam. However, since the Direct Synthesis performance is higher at lower pressures, this mechanical approach is not desirable. The discharge of foaming reaction slurry from the reactor may be avoided by increasing the freeboard (disengagement height) above the liquid level in the reactor. However, this means loss of maximum reactor capacity. Thus, effective and durable use levels can range from 0.001–5 weight percent, depending on the specific antifoam compound used. These percentages are calculated based on the total weight of slurry (solvent, silicon and catalyst precursor) charged to the reactor.

Organofluoropolysiloxanes (fluorosilicones) useful in the present invention contain one or more carbon—fluorine bonds, typically at least two carbon atoms away from the carbon atom bonded directly to silicon. A review of organofluorosiloxane chemistry and applications has been published by B. Boutevin and Y. Pietrasanta in Progress in Organic Coatings, vol. 13 (1985) pp 297–331.

The organofluorosiloxanes of this invention may be linear oligomers and polymers of general formulae: $XR'_2SiO—(SiR'_2O)_k—SiR'_2X$ or cyclic oligomers of general formula, $(R'_2SiO)_n$, or branched oligomers and polymers of the type:

$$\begin{array}{l} XR'_2SiO—(SiR'_2O)_k—(SiR'O)_r—SiR'_2X \\ \qquad\qquad\qquad\qquad\qquad\quad | \\ \qquad\qquad\qquad\qquad\quad (OSiR'_2)_s—SiR'_2X \end{array}$$

in which each R' group is the same different and each is a monovalent hydrocarbon group as defined above for R" groups, provided that at least one R' group is partially or completely substituted with fluorine so as to be a fluorocarbon group. X has the same meaning as R' or is optionally an alkoxy group containing eight or fewer carbon atoms and k, r and s are positive numbers and n is an integer greater than 3. The values of k, n, r and s are chosen such that the fluorosilicone has a normal boiling point that is at least 10° C. higher than the temperature of the Direct Synthesis slurry. In a particular composition, all of the R' groups may be fluorocarbon, or some may be fluorocarbon and the remainder hydrocarbon. The organofluoropolysiloxanes can be used as such, or in foam control compositions containing hydrophobized solids. Suitable organofluoropolysiloxanes include trialkylsilyl endcapped polytrifluoropropylmethylpolysiloxanes with viscosities in the range, 10–60,000 centipoise at 25° C., poly(dimethylsiloxane-co-trifluoropropylmethylsiloxanes) in the same viscosity range. FS 1265, a commercial fluorosiloxane polymer of this structural class having a viscosity of 1000 centipoise at 25° C., is a preferred surface-active additive of this invention.

Other examples of suitable fluorosiloxanes include $(C_8F_{17}C_3H_6SiCH_3O)_n$ $(n \geqq 4)$, $(CH_3)_3SiO$ $(C_4F_9C_2H_4SiCH_3O)_{30}(Si(CH_3)_2O)_{200}Si(CH_3)_3$ and $C_2F_5C_2H_4Si(C_6H_5)_2O(Si(CH_3)_2O)_{100}(SiCH_3C_2H_4C_2F_5O)_5Si(C_6H_5)_2C_2H_4C_2F_5$. Effective use levels of the fluorosiloxane surface-active additives are in the range, 0.00001–5 weight percent, preferably 0.001–0.5 weight percent, based on the total initial weight of the reaction slurry.

ACTIVATION CONDITIONS

Activation is the process of incorporating catalyst, and if desired, other auxiliary agents, into the silicon to make it reactive with the alcohol. Activation may be performed in the same reactor used for the Direct Reaction of the alcohol, or in a separate reactor. In the latter case, the activated silicon is typically and desirably transported to the synthesis reactor in an anhydrous, non-oxidizing atmosphere. Transportation of the activated silicon as a slurry in the reaction solvent is especially preferred.

The present reductive activation is performed between 20°–400° C., preferably between 150°–300° C., with silicon—copper catalyst precursor mixtures containing 0.01–15 weight percent copper, i.e. as the ratio (Cu/(Cu+Si)). Useful reducing agents include $H_2$, CO, $SiH_4$ and mixtures containing them, $H_2$ is the preferred reducing agent. Activation may be performed with the silicon and copper catalyst precursor in their dried state in fluidized bed or fixed bed reactors. Thereafter, the activated silicon is transported to the slurry reactor for reaction with the alcohol. Alternatively, hydrogen or another reducing agent is introduced into an agitated mixture of silicon and copper catalyst precursor in the presence of the reaction solvent. Preferably, the reducing agent is introduced into an agitated mixture of silicon and copper catalyst precursor in alkylated benzene solvents such as NALKYLENE ®550BL, NALKYLENE ®600 L or polyaromatic hydrocarbon solvents such as THERMINOL® 59, THERMINOL ®60 or THERMINOL ®66 or MARLOTHERM® S or MARLOTHERM® L or DOWTHERM® HT. Alcohol is optionally present during the activation with hydrogen. The total quantity of reducing agent must be sufficient to bring about effective activation and avoid significant loss of trialkoxysilane selectivity, and/or formation of undesirable byproducts such as hydrocarbons and water during the Direct Synthesis.

Activation of silicon—copper catalyst precursor mixtures with hydrogen can produce water, alcohols, carboxylic acids and other compounds. These compounds are preferably volatilized so that they are absent prior to the start of the Direct Synthesis of the trialkoxysilanes. If they are present in the synthesis reactor or in the product retention vessel, they can contribute to gel formation, poor reaction selectivity and reduced trialkoxysilane recovery.

The quantity of reducing agent used must be sufficient to generate a catalytically effective copper—activated silicon for the stable, selective and rapid Direct Synthesis of trialkoxysilanes. At a minimum, it must be that quantity which is stoichiometrically required to fully reduce the divalent or monovalent copper to zerovalent copper. Oxidized copper may be present in the bulk catalyst as, for example, in copper (II) hydroxide and copper (I) oxide, or at surfaces as, for example, in copper powders. In practice, many times that amount is used on account of the decreased probability of contact brought about by the greater mass, number and surface area of the silicon particles present in the mixture.

Standard commercial grade hydrogen gas, carbon monoxide or monosilane is suitable for the activation step of the instant invention. Additionally, the hydrogen gas produced as a byproduct of the Direct Reaction of alcohols with silicon is also suitable. As has already been recited hereinabove, this hydrogen gas may contain nitrogen, argon, hydrocarbons and ethers. While it is desirable to remove these other gases, for example by adsorption, prior to recycle of the hydrogen to the activation step, this purification step is not absolutely essential.

Polyaromatic hydrocarbons, for example those described hereinabove as solvents and heat transfer fluids, have been found to be suitable reducing agents for the catalyst precursors of this invention. Reduction of the catalyst precursor, or its mixture with silicon, is carried out in a slurry reactor at temperatures below the boiling point of the polyaromatic hydrocarbon, which is then separated from the solids prior to the Direct Synthesis in alkylated benzene solvents. Following separation, the recovered polyaromatic hydrocarbon can be used again in subsequent reductive activations.

Activation of silicon-copper catalyst precursor mixtures with carbon monoxide (CO) or monosilane ($SiH_4$) is conducted in the same manner as described above for hydrogen. Appropriate safety precautions must be followed in handling $SiH_4$ on account of its pyrophoricity.

The use of hydrogen, carbon monoxide, monosilane and/or polyaromatic hydrocarbons to activate slurries at temperatures below 400° C. is disclosed in a patent application assigned to the assignee of the present application and filed on even date herewith, under internal file number 89603 entitled "Activation of Copper-Silicon Slurries for the Direct Synthesis of Trialkoxysilanes", which is hereby incorporated herein by reference.

REACTION CONDITIONS

Designs, descriptions and operational considerations pertinent to three phase reactors are contained in the following monograph, articles and patents:

A. Ramachandran and R. V. Chaudhari. Three Phase Catalytic Reactors. Gordon and Breach Science Publishers, NY, 1983

N. Gartsman, et al., International Chemical Engineering, vol. 17 (1977) pp 697–702

H. Ying, et al., Industrial & Engineering Chemistry, Process Design & Development, vol. 19 (1980) pp 635–638

N. Satterfield, et al., Chemical Engineering Science, vol. 35 (1980) pp 195–202

M. Boxall, et al., Journal of Metals, (August 1984) pp 58–61

Roeckel, C. Scaccia and J. Conti, U.S. Pat. No. 4,328,175 (May 4, 1982)

M. Litz, U.S. Pat. No. 4,454,077 (Jun. 12, 1984)

Reactors may be operated in a batchwise or continuous mode. In batchwise operation, a single addition of silicon and copper catalyst is made to the reactor at the outset and alcohol is added continuously, or intermittently, until the silicon is fully reacted, or reacted to a desired degree of conversion. In continuous operation, silicon and copper catalyst are added to the reactor initially and thereafter to maintain the solids content of the slurry within desired limits. The batchwise mode is illustrated in U.S. Pat. No. 4,727,173 and the continuous mode in U.S. Pat. No. 5,084,590. Both of these patents are incorporated herein by reference.

In its preferred form in accordance with the present invention, the Direct Synthesis of trialkoxysilanes is conducted in a continuously agitated slurry reactor with an activated silicon—copper catalyst mixture containing a surface-active ingredient capable of controlling foam formation and shortening the interval between onset of the reaction and the attainment of steady-state performance. The reactor may have a single nozzle or multiple nozzles for the introduction of gaseous alcohol. A means of continuous or intermittent addition of activated silicon—copper catalyst mixture, or of silicon, or of surface-active additive is also provided. Means for continuous removal and recovery of the volatile reaction products and unreacted alcohol are also desirably provided. Separation and purification of the trialkoxysilane products are optimally performed in the manner disclosed in U.S. Pat. No. 4,761,492 or U.S. Pat. No. 4,999,446, both of which are incorporated herein by reference.

When the initial loading of silicon and copper catalyst precursor is activated thermally in the reaction solvent or with a reducing gas such as hydrogen, carbon monoxide or monosilane in the presence of a surface-active additive according to the method of the instant invention, continuous slurry phase Direct Synthesis of trialkoxysilanes is advantageously continued by adding only silicon, or silicon containing less copper catalyst than that initially added, and optionally additional surface-active additive. In this way, the copper concentration of the slurry is controlled to minimize the transformation of the alcohol to hydrocarbons and water (Equations 3 and 5 above). Disadvantages caused by water have been recited hereinabove. Foam formation and the time to optimum stable, productivity and selectivity are also minimized.

The reaction is generally conducted at temperatures above about 150° C., but below such a temperature as would degrade or decompose the alcohols or solvents. Preferably, the reaction temperature is maintained in a range from about 200° C. to about 260° C. The reaction of methanol with the copper—activated silicon of the present invention is preferably operated at 220°–250° C., whereas the reaction of ethanol is preferably operated at 200°–240° C. The pressure at which the reaction is conducted is not critical and can be varied from subatmospheric to superatmospheric. Atmospheric pressure is generally employed.

Preferably, the contents of the reaction mixture are agitated to maintain a well mixed slurry of the copper-activated silicon particles and gaseous alcohol in the solvent. The reaction mixture is preferably well insulated to assure that the trialkoxysilane does not reflux. Refluxing can encourage the consecutive reaction of the trialkoxysilane with the alcohol, resulting in loss of the desired trialkoxysilane product by the formation of the tetraalkoxysilane.

At constant temperature, the reaction rate depends on the surface area and particle size of the silicon and on the feed rate of the alcohol. Higher rates are obtained at higher surface areas, finer particle sizes and higher feed rates. These parameters are selected so that a safe, economically sustainable product output is realized without endangerment to people, property and the environment. For example, silicon of 25–75 μ can be used to minimize side reactions and obtain high rates and selectivity to $HSi(OC_2H_5)_3$ at about 230° C., in place of 100–400 μ silicon at about 250° C.

Foaming can be detected visually in glass reactors, or through a sight glass (observation window) in commercial and pilot scale equipment. Occasionally, the first evidence of foaming is the partial or complete transfer of the reaction slurry to the product collection vessel. However, foaming can be detected in opaque equipment by, for example, monitoring the temperature in the line leaving the reactor with well spaced thermocouples. A rapid temperature increase in the outlet line from the reactor is indicative of foaming. Conversely, subsidence of the temperature indicates loss of foam height. It is desirable to operate the reactor with no, or controllably little, foam formation.

PERFORMANCE ADVANTAGES

In accordance with the present invention, the following substantial advantages are realized in the Direct Synthesis of trialkoxysilanes when surface-active additives are present in the reaction slurries.

Shortening of the period between the start of the reaction and the attainment of steady-state rates and selectivities. This leads to an improvement in the yield of trialkoxysilanes and more efficient use of raw materials.

Durable defoaming and antifoaming in the reaction slurries, especially those comprising recycled solvent containing soluble silicates from previous reactions. This leads to more controllable processes and more efficient use of reactor capacity.

DESCRIPTION OF FIG. 1

A schematic drawing of this reactor and its ancillary equipment is shown in FIG. 1. Alcohol is delivered from the reservoir (1) via the pump (2), flow meter (3) and vaporizer (4) to the reactor (5). Separate coils for methanol and the recycle stream are contained within the vaporizer. The reactor contains silicon and copper catalyst precursor suspended and dispersed in a high boiling solvent. A foam control agent is present. Provision is made for nitrogen injection upstream of the vaporizer and hydrogen injection downstream of the vaporizer as shown in the Figure. Alcohol reacts with the copper-activated silicon in the reactor. The reactor is fitted with a hopper (6) for solids, an agitator (7), heater and temperature controller (8), thermocouple bundle (9), internal baffles (10), spargers (11), pressure gauge (12) and pressure release safety valve (13). The gaseous reaction mixture leaves the reactor via the entrainment separator (14). Valve (15) permits sampling of the reaction mixture and venting of water vapor during the hydrogen activation step (16) is an assembly of distillation columns adequate for the separation of unreacted alcohol and lower boilers from the desired trialkoxysilane. The columns are connected to a reboiler (17) and reflux condenser (18). Liquid reaction product (19) containing the desired trialkoxysilane and byproducts with higher boiling points is discharged from the unit to storage containers via the pump (20). The temperatures of the columns and reboiler are controlled such that stream (21) contains the byproduct gases, unreacted alcohol, alkoxysilanes and azeotropes boiling lower than the desired trialkoxysilane. A portion (22) of the liquid overhead stream is returned to the distillation columns as reflux flow. The remainder (23) is recycled through the vaporizer and reinjected into the reactor so that its contained alcohol can be reacted with copper—activated silicon. The vent gas stream (24) is admitted into a flowmeter capable of measuring total gas flow.

EXAMPLES

The following Examples illustrate the preferred embodiments of the instant invention. These are not intended to limit the scope of the invention. Rather, they are presented merely to facilitate the practice of the invention by those of ordinary skill in the art.

ABBREVIATIONS AND UNITS LISTED

Abbreviations used in the presentation of the data of the illustrative examples are the following:

| ABBREVIATION | MEANING | ABBREVIATION | MEANING |
|---|---|---|---|
| TMS | $HSi(OCH_3)_3$ | g | gram |
| TTMS | $Si(OCH_3)_4$ | kg | kilogram |
| TES | $HSi(OC_1H_3)_3$ | L | liters |
| SEL | $HSi(OR)_3/Si(OR)_4$ | micron | |
| % Si/hr | percent silicon converted per hour | $m^2/g$ | square meters per gram |
| N600L | Nalkylene ® 600 L | rpm | revolutions per minute |
| N550BL | Nalkylene ® 550 BL | wt % | weight percent |
| TH59 | Therminol ® 59 | mm | minute |

EQUIPMENT USED

Two laboratory scale Chemineer® reactors of similar design were used in the experiments illustrated hereinbelow. One had a capacity of 3.8 L and the other 5.8 L. A detailed description is given of the 5.8 L reactor and its ancillary equipment. Pilot scale experiments were conducted in a 400 L stainless steel reactor scaled to have the same energy input/volume ratio as the 5.8 L one.

The 5.8 L Chemineer® reactor had four 90° spaced, 1.27 cm wide baffles affixed to its wall. Agitation was provided by two stirrers attached to an axial shaft. The bottom one was a six blade turbine, 6.35 cm in diameter. A four blade propeller of the same diameter was placed 10 cm above the turbine. Power for agitation was provided by a variable speed air-driven motor whose rotational speed was measured by a magnetic tachometer. An electric heating mantle controlled by a heater/temperature controller was used to heat the reactor.

Methanol or ethanol was supplied to the reactor from a 1 L storage container via a calibrated FMI laboratory pump. Coiled stainless steel tubing, 0.32 cm internal diameter×305 cm length, placed in a 4 L silicone oil bath controlled at 150° C. served as the alcohol vaporizer. A similar vaporizer coil was available for the recycle stream, but it was not used during the course of these experiments. The alcohol inlet line entered through the top of the reactor. It was heat traced to prevent condensation of the vapor. Alcohol vapor was injected 2.5 cm from the bottom of the reactor and below the level of the six-blade turbine through a single downward pointing (0.63 cm internal diameter) sparger. A pressure gauge attached the alcohol vapor inlet line gave higher readings (up to about 2 atmospheres) when the sparger was plugged. Ordinarily, the gauge was at zero. Additional alcohol was supplied to the storage container during an experiment to maintain an uninterrupted flow of this reagent.

Reaction products and unreacted alcohol exited the reactor through a 91.4 cm×2.54 cm internal diameter packed tube, which served as entrainment separator and partial distillation column to remove solvent and higher boiling silicates from the product stream. The packing was ceramic saddles and stainless steel mesh. Five thermocouples were distributed along the length of the tube to record temperatures and warn indicate foaming. The lowest thermocouple was flush with the top of the reactor. As was indicated hereinabove, foaming was controlled by the use of FS 1265 and SAG® 100. Flexible tubing connected the outlet of the entrainment separator/partial distillation column to the four-way valve (15 in FIG. 1).

Two ten plate Oldershaw distillation columns served to separate the liquid reaction products and unreacted alcohol from the gases. Effluent from the reactor was admitted into the top of the lower column, which was attached at its lower end to a 3 neck 2 L round bottom flask supported in a heating mantle. The upper column was capped by a magnetically controlled reflux condenser and distillation head with thermocouple. The reflux condenser and another condenser downstream were cooled to −25° C. by circulating silicone oil. Uncondensed gases exited the condenser through a vapor lock bubbler into the total gas flow meter (Model DTM-115. American Meter Co.). Wider tubing was employed downstream of the bubbler to avoid backpressures likely to shatter the glassware (columns, condensers and bubbler) or cause leaks at the joints. A gas sampling port was provided at a T joint following the gas meter. Gas flow from the meter was diluted with nitrogen prior to its discharge into the laboratory hood. A thermocouple was located in the second opening of the three neck flask and the intake to an FMI laboratory pump in the other. The pump was used to transfer liquid product from the flask to Teflon coated polyethylene storage bottles. All glass containers used to store or sample trimethoxysilane and triethoxysilane were washed with dilute HCl, rinsed thoroughly with methanol (or ethanol) and oven dried at 110° C. prior to use.

GENERAL ACTIVATION AND REACTION PROCEDURE

Typically, the 5.8 L reactor was charged with 2 kg solvent, 1 kg silicon, copper catalyst precursor ($Cu(OH)_2$) and 0.6–0.9 g surface-active agent and sealed. According to equation [1], complete conversion of 1 kg silicon will require 3.43 kg methanol (4.93 kg ethanol) and produce 4.36 kg $HSi(OCH_3)_3$ (5.86 kg $HSi(OC_2H_5)_3$) and 873 L $H_2$ at 298K and 1 atmosphere. The slurry was agitated at ~900 rpm and nitrogen introduced as it was heated to 250° C. This temperature was maintained for 0.25—3 hr to permit thorough copper activation of the silicon particles before alcohol was introduced. Longer activation times, for example up to 12 hr. may be used if desired.

Hydrogen pretreatment of the copper-silicon slurry was sometimes employed. When used, hydrogen was injected at 150° C. through the alcohol sparger and its flow maintained for 30 minutes after the final temperature (250° C.) had been reached. The total $H_2$ flow was recorded.

Activation with a polyaromatic hydrocarbon solvent like THERMINOL® 59 is also effective. In practice, the copper (II) hydroxide and THERMINOL® 59 are heated to 180°–250° C. for 0.5–1 hr. optionally in the presence of silicon. The solvent is separated from the copper-containing solids, which are then dispersed in another solvent like NALKYLENE® 550 L along with silicon to form a slurry for the Direct Synthesis.

During activation, gas flow from the reactor was vented through the four-way valve and not admitted to the distillation columns until just prior to the initiation of alcohol flow. Simultaneous with activation, the alcohol vaporizer was heated to ~150° C. and the refrigerant circulated through the reflux condenser was cooled to −25° C. Alcohol flow to the reactor was initiated when gas chromatographic analysis of the effluent stream (24 in FIG. 1) showed that there was only nitrogen in the vent gas. Of course, comparative experiments (see Example ?) were run without the addition of a surface-active agent.

Once the alcohol flow was underway, sampling and analysis of the vent gas stream (24 in FIG. 1) for hydrogen were done every 10–15 minutes until a stable composition was established. That indicated the end of the induction period. Thereafter, gas sampling was done every 30 minutes to monitor hydrogen, hydrocarbons and ethers. During the course of the reaction, total vent gas flow was used as an approximate measure of the reaction rate according to the stoichiometry of equation (1).

Samples were collected in acid washed, alcohol rinsed, dried refrigerated containers attached at the four-way sampling valve (15 in FIG. 1) for 2–5 minutes every half hour. They were weighed and analyzed by gas chromatography. The bulk of the liquid product was condensed in the three neck flask which served as the reboiler (17 in FIG. 1) and transferred to storage. All of these data were used to calculate the temporal composition of the product stream, its selectivity to trialkoxysilane, the reaction rate and overall silicon conversion. Usually, reactions were terminated after >85% of the silicon charged to the reactor had been reacted. In some cases, terminations were made at lower and higher silicon conversions depending on the objective of the experiment.

Gas samples were analyzed for hydrogen, nitrogen and hydrocarbons (e.g. methane, ethane) content on a Hewlett Packard 5840 gas chromatograph fitted with a GS-Molesieve 30 m×0.53 mm internal diameter (J & W Scientific) capillary column and flame ionization detector. Argon was the carrier gas. Gas chromatography-mass spectrometry was used to analyze for dimethyl ether. Liquid samples containing alkoxysilanes were analyzed on a Hewlett Packard 5890 gas chromatograph with a 3.66 m×3.18 mm stainless steel column packed with 20% OV-101 on 60/80 mesh Chromosorb (Supelco).

Used solvent was analyzed by gravimetry and atomic absorption spectrometry for total silicon content and by $^{29}Si$ NMR for the speciation of the soluble silicon into $Q^0$, $Q^1$, $Q^2$, $Q^3$ and $Q^4$ groups. The chemical shifts (relative to tetramethylsilane) of these functional groups are set forth below.

| GROUP | STRUCTURE | $^{29}Si$ NMR SHIFTS (ppm) |
|---|---|---|
| Q0 | $Si(OR)_4$ | −78.3 to −78.5 |
| Q1 | O—$Si(OR)_3$ | −85.6 to −85.9 |
| Q2 | O—$Si(OR)_2$—O | −93.6 to −93.9 |
| Q3 | O—Si—O(OR)O | −102.0 to −102.6 |
| Q4 | $SiOSi_4$ | −110 |

Molar percentages of these groups are calculated from the integration areas.

MATERIALS USED

Technical grade silicon samples utilized in the experiments of the illustrative Examples are listed in Table 1 along with relevant analytical data. Silicon samples used in Examples 1, 2, 3 and 5 satisfied the composition ranges and particle size distribution given below for Si-1. Silicon sample Si-2 was used in Example 4. All samples contained minimally 98.5 wt % Si. Table 2 presents a data summary for the copper hydroxide catalysts used. NALKYLENE® 550 BL, NALKYLENE® 600 L, THERMINOL® 59, THERMINOL® 66 and MARLOTHERM® S were the solvents used. FS 1265 (Dow Corning) and SAG® 100 (OSi Specialties) were the surface-active additives.

TABLE 1

COMPOSITION OF SILICON SAMPLES USED IN ILLUSTRATIVE EXAMPLES

| ELEMENT | SAMPLE Si-1 | SAMPLE Si-2 |
|---|---|---|
| Al, wt % | 0.2–0.35 | 0.08 |
| Ba, ppm | 13.4 | <3 |
| Ca, ppm | 130–517 | 600 |
| Cr, ppm | 25–100 | 58.9 |
| Cu, ppm | 19–50 | 34.8 |
| Fe, wt % | 0.25–0.65 | 0.38 |
| Mg, ppm | 20–100 | 8.8 |
| Mn, ppm | 100–300 | 90.4 |
| Ni, ppm | <10 | 15.5 |
| P, ppm | 25–50 | 26.8 |
| Pb, ppm | <10 | <10 |
| Sn, ppm | <10 | <10 |
| Ti, ppm | 310–501 | 299 |
| V, ppm | 20–100 | 14.3 |
| Zn, ppm | <10 | <5 |
| Zr, ppm | 100–300 | 29 |
| Si | Balance | Balance |

PARTICLE SIZE DISTRIBUTION OF SILICON SAMPLES USED IN ILLUSTRATIVE EXAMPLES

| NOMINAL SIEVE SIZE. μ | Wt % > NOMINAL SIZE. Si-1 | Wt % > NOMINAL SIZE. Si-2 |
|---|---|---|
| 600 | 0 | 3.1 |
| 425 | 0 | 14.0 |
| 300 | 1.6 | 18.7 |
| 250 | 28.4 | 13.7 |
| 180 | 30.3 | 11.9 |
| 75 | 39.5 | 24.1 |
| <75 | 0.1 | |
| 45 | | 1.5 |
| <45 | | 11.6 |

TABLE 2

CHARACTERIZATION OF COPPER (II) HYDROXIDE CATALYST USED IN ILLUSTRATIVE EXAMPLES

| PROPERTY | VALUE |
|---|---|
| Cu, wt % | 57.50–58.5 |
| Al, ppm | 250–1000 |
| As, ppm | <30 |
| Ca, wt % | 0.11–0.22 |
| Fe, ppm | 120–2000 |
| P, wt % | 1.5–1.8 |
| Pb, ppm | 100–300 |
| Sb, ppm | 20–100 |
| Sn, ppm | <50–100 |
| Zn, wt % | 0.03–0.2 |
| $H_2O$ wt % | <1.0–10 |
| $Cl^{31}$, ppm | 110–350 |
| $SO_4^{3-}$, wt % | 0.5–3 |
| Surface Area, $m^2/g$ | 20–40 |
| Particle Size Range, μ | 0.1–20 |

EXAMPLE 1

This Example illustrates the use of SAG® 100 compound as a defoamer and antifoam during the Direct Synthesis of $HSi(OCH_3)_3$.

The experiment was performed in the 3.8 L Chemineer® reactor with 1.4 kg THERMINOL® 66, 700 g silicon Si-1 and 4.6 g $Cu(OH)_2$. The slurry was stirred (800 rpm) and heated to 220° C. in the presence of flowing nitrogen to activate the silicon-copper solids for reaction. The level of the stirred slurry was ~75% of the height of the reactor.

Methanol was introduced at 6 g/min after the reaction slurry had been at 220° C. for about 40 minutes. Temperatures recorded along the packed entrainment separator/partial distillation column attached to the exit of the reactor are set forth in Table 3. Thermocouple 1 (T1) was at the same level as the top of the reactor and thermocouple 5 (T5) was farthest away from it. Data are shown only for three of the five recording thermocouples.

When, after about 3.5 hr, the T1 temperature jumped from −122° C. to 181° C., it was apparent that hot reaction slurry had climbed to the top of the reactor. Reduction of the methanol flow rate to 4 g/min and even to 2 g/min after 4.5 hr and 5.5 hr, respectively, did not effect foam subsidence. T1 registered 199.6° C. at 5.8 hr, just prior to the injection of 0.5 g SAG® 100 into the hot reaction slurry. That defoaming was practically instantaneous was indicated by the sudden temperature drop at T1 to 118°–120° C. Methanol flow was increased again to 6 g/min and the reaction was continued for another 2 hr with no further temperature jump at T1.

TABLE 3

EVIDENCE OF FOAMING AND ITS CONTROL WITH SAG ® 100 IN THE DIRECT SYNTHESIS OF $HSi(OCH_1)_2$

| TIME. hr | REACTOR TEMP. ° C. | T1, ° C. | T3 ° C. | T5, ° C. | NOTES |
|---|---|---|---|---|---|
| 0 | 219 | 69.6 | 59.2 | 35 | Start $CH_3OH$ 6 g/min |
| 0.75 | 219 | 126.2 | 83.6 | 75.4 | |
| 1.5 | 220 | 117.3 | 83.2 | 73.7 | |
| 2.0 | 220 | 121.7 | 83.1 | 72.9 | |
| 2.5 | 220 | 121.7 | 83.1 | 72.9 | |
| 3.5 | 222 | 181.0 | 80.8 | 70.3 | Foaming |
| 4.5 | 218 | 187.5 | 77.0 | 67.4 | $CH_3OH$ 4 g/min |
| 5.5 | 219 | 199.6 | 78.0 | 65.7 | $CH_3OH$ 2 g/min |
| 5.8 | 220 | 199.6 | 85.1 | 65.7 | 0.5 g SAG ® 100 |
| 6.5 | 220 | 118.0 | 78.0 | 74.9 | No Foaming |
| 7.5 | 223 | 120.0 | 76.1 | 67.9 | No Foaming |

These data indicate that, in the absence of a foam control additive, foaming probability increases with reaction time. Soluble silicate concentrations in the reaction slurry increase with time and might contribute to foaming. SAG® 100 effectively reduced or eliminated foam formation when it was added during the course of the reaction.

EXAMPLES 2A–C

This Example illustrates the reduction of the time to attain steady-state selectivities brought about by the addition of the surface-active additives, SAG® 100 and FS 1265, to the reaction slurry at the outset of the Direct Synthesis.

Three reactions are summarized in this Example. Each was run in the 5.8 L Chemineer reactor at 250° C. and 800 rpm with a slurry containing 2.14 kg THERMINOL® 59, 1.07 kg silicon Si-1, 7.06 g $Cu(OH)_2$ and $CH_3OH$ feed rate, 3 g/min. The stirred slurry level was ~50% of the total reactor height. Whereas Example 2A was run without the addition of surface-active agent, 0.64 g SAG® 100 was added to the slurry of Example 2B and 0.64 g FS 1265 was added to the slurry of Example 2C at the outset of the experiments. All three slurries were activated thermally by heating to 250° C. in the presence of bubbling nitrogen. Temperature increases along the entrainment separator/partial distillation column similar to those reported in Example 1 were not observed in these experiments on account of the longer disengagement zone in 5.8 L reactor.

Reaction performance is summarized in Table 4. Table 4 shows that, in Example 2A, 5 hours elapsed before the experiment produced samples having approximately constant (~80–85 wt %) levels of $HSi(OCH_3)_3$. Stable (~85–88 wt %) values were already realized in the experiment of Example 2B within 2 hours. Three hours were required in Example 2C to attain 79–83 wt %. Total weights of crude $HSi(OCH_3)_3$ in Examples 2B and 2C exceeded that in Example 2A by 100–200 g. These improvements were effected by 20 parts per million SAG® 100 or FS 1265 based on the total initial weight of the slurry.

TABLE 4

YIELD IMPROVEMENTS AND REDUCTION IN TIME TO STEADY STATE SELECTIVITY CAUSED BY 20 ppm SAG ® 100 AND FS 1265 IN $HSI(OCH_3)_3$ DIRECT SYNTHESIS

| Surface-active Additive TIME, hr | EXAMPLE 2A None TMS, wt % | EXAMPLE 2B SAG ® 100 TMS, wt % | EXAMPLE 2C FS 1265 TMS, wt % |
|---|---|---|---|
| 1 | 50.77 | 68.05 | 61.88 |
| 2 | 61.26 | 87.07 | 66.60 |
| 3 | 68.61 | 85.15 | 79.25 |
| 4 | 80.45 | 86.24 | 82.30 |
| 5 | 84.89 | 87.66 | 83.26 |
| TotalWeight of Crude Product, kg | 1.03 | 1.23 | 1.14 |

EXAMPLES 3A–B

This Example illustrates that the fluorosiloxane, FS 1265, is an effective and durable antifoam in the Direct Synthesis of $HSi(OCH_3)_3$ when an alkylated benzene (N550BL) or mixture of diphenyl ethanes (TH59) is the reaction solvent and the reaction slurry is activated with hydrogen.

The slurry of Example 3A was prepared in the 5.8 L reactor with 1 kg silicon (Si-1), 2 kg N550BL, 7.05 g $Cu(OH)_2$ and 0.6 g FS 1265. That of Example 3B contained 2 kg TH59 in place of N550BL. In each case, hydrogen was introduced when the temperature of the slurry was 150° C. and its flow maintained for 30 minutes after the temperature reached 250° C. Total hydrogen usage was 451.3 L in Example 3A and 1803.9 L in Example 3B. On a molar basis, these volumes far exceeded the 0.064 mole (1.56 L) required to reduce the 7.05 g copper catalyst charged to the reactor. This excess was necessary because of the larger mass and surface area of silicon particles relative to copper (II) hydroxide in the slurry.

A nitrogen sparge was used to eliminate hydrogen from the reactor before methanol was introduced. This was done so that only hydrogen produced as a result of the methanol+activated silicon reaction would be measured in the vent gas. Methanol flow was 3.3 g/min. Vent gas samples were analyzed by gas chromatography every 10–15 minutes following the start of methanol flow until the area ratio of hydrogen to nitrogen attained a stable value. $H_2$=92 area %, $N_2$=8 area % was observed within 90 minutes and remained within ±0.5 area % of these values for greater than 23 hr in both experiments. The slurries remained contained within the reactor during the course of both reactions. There was no visible or temperature indication of foaming.

92–94 wt % of the silicon charged was converted to crude reaction product in both Examples. The reaction of Example 3A produced a total of 4.8 kg crude product containing 3.78 kg $HSi(OCH_3)_3$ and 0.31 kg $Si(OCH_3)_4$, while that of Example 3B produced 5.3 kg crude containing 3.93 kg $HSi(OCH_3)_3$ and 0.13 kg $Si(OCH_3)_4$. Soluble silicon in the spent slurry of Example 3A was 0.5 wt %. $^{29}Si$ NMR disclosed the following speciation of silicate groups: $Q^0$=3.3 mole %, $Q^1$=62.8 mole %, $Q^2$=33.9 mole %. The spent slurry of Example 3B contained 0.16 wt % soluble silicon and had very weak $^{29}Si$ NMR signals.

EXAMPLE 4

This Example illustrates the Direct Synthesis of $HSi(OC_2H_5)_3$ in the solvent MARLOTHERM® S with and without the fluorosiloxane, FS1265. The hydrogen activated slurries of both experiments were initially reacted with methanol before the reactions were continued with ethanol.

In Example 4A, the reaction slurry contained 0.8 g FS 1265. No surface-active agent was intentionally added to the experiment of Example 4B. Otherwise, each of the two experiments of this Example was conducted with 1 kg silicon (Si-2). 14.1 g $Cu(OH)_2$ and 2.1 kg MARLOTHERM® S. Each slurry was activated with hydrogen as described in the general procedure above. A total of 1403.8 L $H_2$ was introduced in Example 4A and 1259 L $H_2$ in Example 4B between 150°–250° C. over a period of 65 minutes. With the temperature at 250° C. in both experiments, methanol was introduced at 4.3 g/min and its flow maintained for 5 hours. In that time, ~20% silicon was converted primarily to $HSi(OCH_3)_3$ and $Si(OCH_3)_4$.

After the reactor temperature had been lowered and stabilized at 230° C., ethanol was introduced at 4.3 g/min. Nitrogen flow was maintained during the temperature drop. No $H_2$ was present in the vent gas just prior to the start of the ethanol feed. Vent gas analysis 10–15 minutes after the initiation of ethanol flow showed the presence of $H_2$. In Example 4A, gas chromatographic analysis of the vent gave stable values of $H_2$=85 area %, $N_2$=15 area % and in Example 4B $H_2$=76 area %. $N_2$=24 area % after about 30 minutes.

The liquid reaction products were analyzed periodically for $HSi(OC_2H_5)_3$, $Si(OC_2H_5)_4$ and other byproducts. That from Example 4A contained ~80 wt % $HSi(OC_2H_5)_3$, ~20 wt % $C_2H_5OH$ and a trace of $Si(OC_2H_5)_4$ after 60 minutes. Trialkoxysilane yield was 558 g $HSi(OC_2H_5)_3$ within 4.5 hr. In contrast, liquid product from the experiment of Example 4B contained ~60 wt % $HSi(OC_2H_5)_3$ and ~40 wt % $C_2H_5OH$ after 60 minutes. The reaction produced 380.5 g $HSi(OC_2H_5)_3$ in 4.5 hr.

The higher content of $H_2$ in the vent gas of the experiment of Example 4A was indicative of a higher $HSi(OC_2H_5)_3$ production rate brought about by the presence of the fluorosilicone in the reaction slurry. Although, both reactions attained steady-state in about 30 minutes, the slurry containing FS 1265 was producing 20 wt % more $HSi(OC_2H_5)_3$ than the one without this surface-active additive.

EXAMPLE 5

This Example illustrates the occurrence and control of foaming during the Direct Synthesis of $HSi(OCH_3)_3$ in the 400 L stainless steel pilot scale reactor at 250° C. and 400 rpm.

The reactor was charged with 136 kg THERMINOL® 59, 68 kg silicon (Si-1), 0.45 kg $Cu(OH)_2$ and 231 kg methanol. This mixture was slurried at 400 rpm and heated to 250° C. with a nitrogen sparge. This thermal activation was continued for 3.25 hr. Thereafter, methanol flow was initiated at 7.7 kg/hr and increased in stages up to 11.8 kg/hr. Foam formation was monitored visually through the observation window at the top of the reactor.

With fresh THERMINOL® 59, or that which had been treated for removal of soluble silicates by the process of U.S. Pat. No. 5,166,384, foaming was initially not observed even at the highest methanol flow rates. When the THERMINOL® 59 had been used in previous reactions and the soluble silicates had not been removed, foaming was sometimes observed even at the lowest (7.7 kg/hr) methanol flow rate. In most cases, there was no carryover of foam into the distillation columns because the reactor was designed with a long disengagement height.

In one experiment with a previously used batch of solvent which had been centrifuged at 1000 rpm for particulate separation, but not chemically treated for soluble silicate removal, foaming was visible when the methanol flow rate was increased from 7.7 kg/hr to 9.1 kg/hr. A solution containing 66 g FS 1265 in 594 g THERMINOL® 59 was then injected into the reactor and the response observed through the observation window. Defoaming was instantaneous and vapors were observed to rise from the surface of the slurry to the reactor outlet. No additional foaming occurred during the ensuing hours of reaction at methanol flow rates of 9.1–11.8 kg/hr. The quantity of FS 1265 used was equivalent to 322 parts per million based on the total weight of slurry. Untreated solvent from this experiment was recycled, without further purification, to the reaction of three additional 68 kg batches of silicon. Foaming was not observed in any of these runs. Subsequent experiments showed that FS 1265 concentrations as low as 50, 100 and 200 parts per million can provide effective and durable defoaming action in the 400 L reactor.

What is claimed is:

[1. A process for producing trialkoxysilane of the formula $HSi(OR)_3$ wherein R is an alkyl group containing 1 to 6 carbon atoms inclusive, comprising (a) slurrying silicon metal in a thermally stable solvent in the presence of a surface-active additive and of a catalyst precursor which is halogen-free and which comprises copper, (b) activating said catalyst precursor, thereby generating a catalyst for the reaction of step (c), and (c) reacting said silicon metal with an alcohol of the formula ROH in the presence of the catalyst generated in step (b) to form said trialkoxysilane; wherein said surface-active additive comprises (i) a mixture of (i)(A) hydrophobized silica particles with average particle sizes in the range of 0.2–5 microns, and specific surface area between 50 and 400 square meters per gram and (i)(B) an organopolysiloxane selected from the group consisting of compounds of the general formula: $R''_3SiO—(SiR''_2O)_a—SiR''_3$, cyclic compounds of the general formula: $(R''_2SiO)_b$, branched oligomers and polymers of the formula $$R''_3SiO—(SiR''_2O)_k—(SiR''O)_r—SiR''_3$$
$$\qquad\qquad\qquad\qquad\quad |$$
$$\qquad\qquad\qquad\qquad (OSiR''_2)_s—SiR''_3$$

and mixtures thereof, wherein R" in each occurrence is the same or different and each is a $C_1$–$C_{20}$ alkyl group, phenyl, alkyl-substituted phenyl, cycloalkyl, or alkyl-substituted cycloalkyl; a, b, k, r and s are greater than zero and have values such that the normal boiling point of the organopolysiloxane is at least 10° C. higher than the temperature of the Direct Synthesis slurry; wherein the weight ratio of (i)(A) to (i)(B) is 1:99 to 99:1, or (ii) an organofluorosiloxane selected from the group consisting of compounds of the general formula $XR'_2SiO—(SiR'_2O)_k—SiR'_2X$, cyclic compounds of the general formula $(R'_2SiO)_n$, branched oligomers and polymers of the formula $$\begin{array}{l} XR'_2SiO—(SiR'_2O)_k—(SiR'O)_r—SiR'_2X \\ \qquad\qquad\qquad\qquad\quad | \\ \qquad\qquad\qquad\qquad (OSiR'_2)_s—SiR'_2X \end{array}$$

and mixtures thereof, in which R' has the same meaning as R", provided that at least one R' group is wholly or partially substituted with fluorine, X has the same meaning as R' or is optionally an alkoxy group containing eight or fewer carbon atoms, and k, r and s are positive numbers, n is an integer greater than 3, and the values of k, n, r and s are chosen such that the fluorosilicone has a normal boiling point that is at least 10° C. higher than the temperature of the slurry at which step (c) is carried out.]

2. The process of claim [1] *19* wherein R is methyl.

3. The process of claim [1] *19* wherein R is ethyl.

4. The process of claim [1] *19* wherein said catalyst precursor comprises one or more copper(I) compounds.

5. The process of claim [1] *19* wherein said catalyst precursor comprises one or more copper(II) compounds.

6. The process of claim [1] *19* wherein said catalyst precursor comprises copper(II) hydroxide.

7. The process of claim [1] *19* wherein the slurry formed in step (a) contains alcohol of the formula ROH.

8. The process of claim [1] *19* wherein in step (a) said solvent comprises polyaromatic hydrocarbons, and said catalyst precursor is activated in step (b) by heating in said solvent, and said step (c) is carried out in a solvent comprising alkylated benzene.

9. The process of claim [1] *19* wherein step (b) comprises fully reducing to $Cu^0$ copper in said catalyst precursor which is not fully reduced.

10. The process of claim 9 wherein step (b) is carried out by reacting said catalyst precursor with gaseous hydrogen.

11. The process of claim 9 wherein step (b) is carried out by reacting said catalyst precursor with carbon monoxide.

12. The process of claim 9 wherein step (b) is carried out by reacting said catalyst precursor with $SiH_4$.

13. The process of claim 9 wherein step (b) is carried out by reacting said catalyst precursor with an organosilane containing one or more SiH groups.

14. The process of claim 9 wherein step (b) is carried out by reacting said catalyst precursor with an organosilane containing one or more $SiH_2$ groups.

15. The process of claim 9 wherein step (b) is carried out by reacting said catalyst precursor with an organosilane containing one or more $SiH_3$ groups.

16. The process of claim 9 wherein the slurry formed in step (a) contains alcohol of the formula ROH.

17. The process of claim 9 wherein hydrogen is formed in the reaction of step (c) and all or a portion of said hydrogen is recycled to step (b) and is used in the reduction of step (b).

18. The process of claim 9 wherein in step (a) said solvent comprises polyaromatic hydrocarbons, and said catalyst precursor is reduced in step (b) by heating in said solvent, and said step (c) is carried out in a solvent comprising alkylated benzene.

*19. A process for producing trialkoxysilanes of the formula $HSi(OR)_3$, wherein R is an alkyl group containing 1 to 6 carbon atoms inclusive, comprising the steps of:*

*(a) slurrying silicon metal in a solvent in the presence of a surface-active additive and of a catalyst precursor which comprises copper;*

*(b) activating said catalyst precursor, thereby generating a catalyst for the reaction of step (c); and*

*(c) reacting said silicon metal with one or more alcohols of the formula ROH in the presence of the catalyst generated in step (b) to form said trialkoxysilanes;*

*wherein said surface-active additive comprises hydrophobized solid particles and*

*(i) an organopolysiloxane selected from the group consisting of compounds of the general formula $R''_3SiO—(SiR''_2O)_a—SiR''_3$, cyclic compounds of the general formula $(R''_2SiO)_b$ branched oligomers and polymers of the formula*

$$\begin{array}{l} R''_3SiO—(SiR''_2O)_k—(SiR''O)_r—SiR''_3 \\ \qquad\qquad\qquad\qquad\quad | \\ \qquad\qquad\qquad\qquad (OSiR''_2)_s—SiR''_3 \end{array}$$

*and mixtures thereof, wherein R" in each occurrence is the same or different and each is a $C_1$–$C_{20}$ alkyl group, phenyl, alkyl-substituted phenyl, cycloalkyl, or alkyl-substituted cycloalkyl; a, b, k, r and s are greater than zero and have values such that the organopolysiloxane has a normal boiling point that is at least 10° C. higher than the temperature of the slurry during the reaction of step (c); or*

*(ii) an organofluorosiloxane selected from the group consisting of compounds of the general formula $XR'_2SiO—(SiR'_2O)_k—SiR'_2X$, cyclic compounds of the general formula $(R'_2SiO)_n$ branched oligomers and polymers of the formula*

$$\begin{array}{l} XR'_2SiO—(SiR'_2O)_k—(SiR'O)_r—SiR'_2X \\ \qquad\qquad\qquad\qquad\quad | \\ \qquad\qquad\qquad\qquad (OSiR'_2)_s—SiR'_2X \end{array}$$

*and mixtures thereof, wherein R' in each occurrence is the same or different and has the same meaning as R" provided that at least on R' group is wholly or partially substituted with fluorine, X has the same meaning as R' or is optionally an alkoxy group containing eight or fewer carbon atoms, and k, r, and s are positive numbers, n is an integer greater than 3, and the values of k, n, r and s are chosen such that the organofluorosiloxane has a normal boiling point at least 10° C. higher than the temperature of the slurry during the reaction of step (c);*

*or mixtures of (i) and (ii).*

*20. The process of claim 19, wherein the hydrophobized solid particles are silica.*

*21. The process of claim 19, wherein the catalyst precursor is halogen-free.*

*22. The process of claim 19, wherein hydrophobized solid particles have an average particle size in the range of 0.2–5 microns.*

*23. The process of claim 19, wherein hydrophobized solid particles have a specific surface area between 50 and 400 square meters per gram.*

* * * * *